United States Patent [19]

Pernia et al.

[11] Patent Number: 5,634,945
[45] Date of Patent: Jun. 3, 1997

[54] BIOLOGICAL FILLER AND USE OF SAME

[76] Inventors: Luis R. Pernia, 350 39th St., Northport, Ala. 35476; Garbis Kaakedjian, Av. Andres BE1/0, Sector Las Palmas, Edif Rubi Apt. 10-A, Caracas, Venezuela

[21] Appl. No.: 397,853

[22] Filed: Mar. 2, 1995

[51] Int. Cl.⁶ .................................................. A61F 2/02
[52] U.S. Cl. .................................................. 623/11
[58] Field of Search .................. 623/8, 11, 66, 623/901, 15; 132/201; 446/394

[56] References Cited

U.S. PATENT DOCUMENTS

| | | | |
|---|---|---|---|
| 1,364,366 | 1/1921 | Goldman | 132/53 |
| 2,865,380 | 12/1958 | Mitchell | 132/53 |
| 3,119,398 | 1/1964 | Bennett et al. | 132/201 |
| 5,358,935 | 10/1994 | Smith et al. | 623/11 |

*Primary Examiner*—Robert A. Clarke
*Attorney, Agent, or Firm*—Veal & Associates

[57] ABSTRACT

This biological replacement material for soft tissues utilizes hair clipped in advance of the surgery and properly treated to insure that no biological micro-organisms or other contaminants are on the hair. The harvested hair is cut to an appropriate length, whereupon it may be woven, encapsulated or otherwise combined with a physiologically degradable material to form the hair into an anatomically useful structure.

10 Claims, 1 Drawing Sheet

BIOLOGICAL FILLER AND USE OF SAME

FIELD OF THE INVENTION

The present invention relates to the treatment of soft tissue in the body and more particularly relates to the replacement of soft tissue. In greater particularity, the present invention is a soft tissue replacement material and the method for use of the same. In still greater particularity, the present invention relates to the use of a biological replenishable material as the replacement material. Specifically, the present invention relates to the use of hair as the material for soft tissue replacement surgery.

BACKGROUND

Restorative surgery has long had the difficult task of finding replacement materials for use as fillers, grafts and connectors in the practice of the specialty. In this practice, as well as in many other aspects of medicine, the body's superbly designed defense mechanisms present a challenge to the physician's task of intervening and manipulating the body tissue to achieve a functional or an aesthetically pleasing result. To date, different methods of replacement of tissue and different replacement materials have been widely used, however, they have been, to a certain extent, unsatisfactory. Evidence of the unsatisfactory result is shown by the history of the use of silicon in breast implants. In addition to the variety of medical problems reported by the implantees of such devices, silicones are known to be problematic due to capsular contraction.

Another form of replacement has been the use of dermal fat grafts; however, such grafts have a tendency for resorption, leaving the graftee in little better condition than before the procedure. The use of bovine collagen has been attempted, but such attempts bring their own peculiar set of worries.

A soft tissue replacement for defects should have certain characteristics, including freedom from rejection, such that the body's defenses are minimized as a problem. The material should be persistent, malleable, of easy use, and free of complications from its use. Additionally, it should be of low cost.

SUMMARY OF THE INVENTION

The principal object of the present invention is to enable the surgeon to repair a defect or injury using a material to replace tissue missing from a particular location on the patient.

As an adjunct to the principal object, it is a further object of the invention to provide a material for use as a replacement for soft tissue which is available, cost effective, and not likely to suffer rejection or complications from its use. A further object of the invention is to provide a replacement material which can provide mass as well as structure for interstitial integration with the surrounding tissue.

These, and further objects and advantages of our invention, are accomplished by using a material that is generally prevalent and is replenishable. The base material is hair that can be taken from the patient into which it is to be implanted, or from others. Hair is formed by a protein conglomerate, and its antigens and antibodies are the same as the rest of the body. Accordingly, hair and especially autologous hair should not suffer rejection by the body; thus, in the invention, hair is used either from the patient or from donors. In advance of the surgery, the hair is properly treated to insure that no biological micro-organisms or other contaminants exist. The hair is cut to an appropriate length, whereupon it may be woven, encapsulated, or otherwise combined with a physiologically degradable material to form the hair into an anatomically useful structure.

BRIEF DESCRIPTION OF THE DRAWINGS

The accompanying drawings depict our invention in use and form a portion of this disclosure as follows.

DESCRIPTION OF A PREFERRED EMBODIMENT

Figures 1, 2:
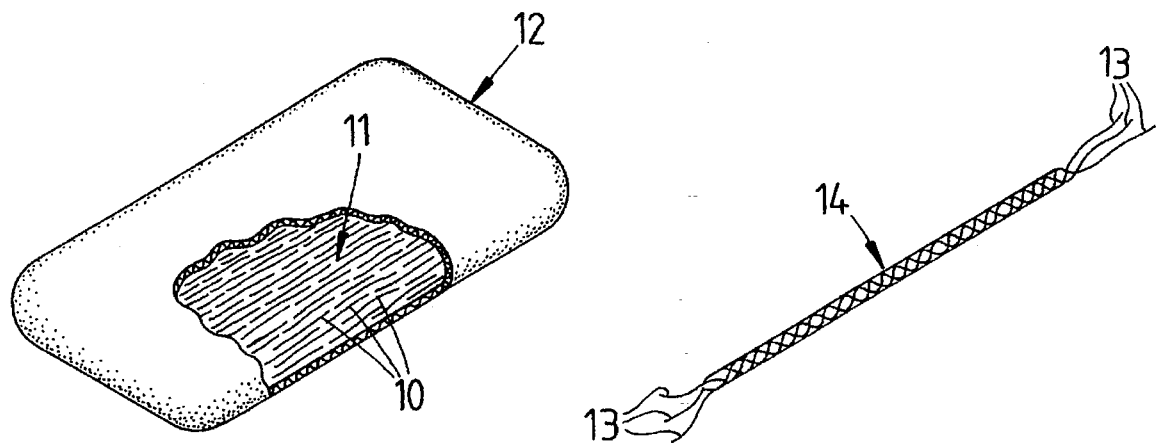
FIG. 1 is a partial sectional view of a mass of hair encapsulated for use as an implant.
FIG. 2 is a perspective view of a connective strand made from harvested hair and a physiologically degradable substance.

Referring to the Drawings for a clearer understanding of the invention, it should be understood that the current invention is not to hair or autologous hair as it appears, for example, on the human head. The hair on one's head, although routinely shampooed and neatly combed, is far from being an acceptable filler material, inasmuch as the hair is a repository for numerous micro-organisms which may adversely affect the use of the hair as a medical implant. Likewise, one's hair may be subject to remnants of numerous cosmetic preparations placed thereon and is generally a repository of minute airborne contaminants of various descriptions. Consequently, the present disclosure is not directed to "hair" which has not been harvested and appropriately treated.

Our invention contemplates the use of hair as a replacement filler or structure substitute in situations wherein the subject patient has had a loss of tissue mass or was born with a defect of insufficient mass, or in some instance, simply finds that increased soft tissue in certain areas of the anatomy would be physiologically and psychologically beneficial. Accordingly, the patient will normally be prepared for the surgery, and, at some point in advance thereof, a quantity of hair can be harvested from the patient's head or the head of another person. Harvesting requires cutting the hair shaft to sever the hair follicle from the root, which remains intact. Accordingly, the harvesting may be less traumatic to the patient than a bad haircut.

Subsequent to harvesting, the hair must be ridden of all the potential contaminants: accordingly, the harvested hair should be sterilized, such as by boiling or steam treatment to raise the temperature and separate all undesirable oils, greases, and residues, and to remove any minute organic or inorganic contaminants. After sterilization, the hair is washed in a non-ionic detergent to further remove any contamination left by the sterilization process. Finally, the harvested hair is washed carefully with an isotonic salt solution to eliminate possible microorganism bacteria and other substances that could be the cause of infection or antigenic activity.

The harvested hair may be sized according to the use thereof. For example, the hair may be clipped into short lengths 10, similar to staple cut in textile processing, and the short lengths 10 may be formed into a mass 11, with the lengths within the mass having no uniform orientation. As such, the hair may be flowable and may be injected with a cannula within a small defined cavity beneath the skin until a quantity of hair sufficient to provide a malleable mass is contained within the cavity. The external opening to the cavity is sutured closed. Alternatively the mass 11 of hair may be encapsulated, as shown in FIG. 1, in a pouch 12 made of a medically acceptable material; for example, the same type material as used in the absorbable sutures. The pouch may take on the desired shape and size for the implant; for example, in a breast implant, the pouch and hair mass may be formed anatomically correctly prior to the surgery for the specific patient using the patient's own hair.

In another embodiment, the harvested hair may be cut into longer lengths 13, as shown in FIG. 2, and braided, or in some manner woven, to form a strand 14 having multiple long lengths 13 of the harvested hair. The strands may be secured at the ends with a surgical steel clip and may find use in situations where a connective strand has been injured or lost to disease or trauma. It should be understood that the strand 14 may be a composite of hair and a physiologically degradable material such as the aforementioned suture material.

Figures 3, 4:
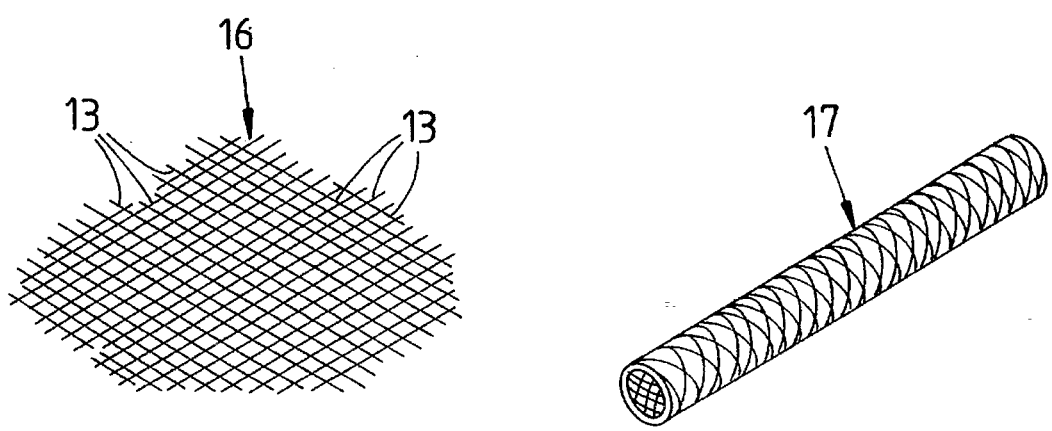
FIG. 3 is a perspective view of a fabric of harvested hair.
FIG. 4 is a perspective view of a tube of harvested hair.

In yet another embodiment, the harvested hair in the form of long lengths 13 may be woven to form a mat 16 as shown in FIG. 3, with the lengths extending longitudinally and transversely. Such mats may be used at graft locations to serve as a base for interstitial collagen development. Mats using harvested hair may ostensibly be used in the various procedures currently performed using synthetic materials. Again, depending on the needs of the surgery, the mat may be formed, in part, from a physiologically absorbable material.

In a variation on the last described embodiment, it is known to use synthetic tubular woven materials in the grafting of blood vessels and the like wherein the tubular mat serves as the base on which new tissue grows. In FIG. 4, we illustrate a tubular member 17 formed from harvested hair of an appropriate length which may have the desired inner diameter and may be used instead of the synthetic grafts currently in use. Again, the member 17 may be a composite material including the harvested hair and an absorbable material as used in absorbable sutures and surgical glue.

It will be appreciated that in each instance the fiber must remain in situ and retain characteristics similar to the soft tissue it has replaced. To test this method and material we have conducted animal studies as hereinafter described. In Study I, ten pure bred Lewis rats, age eight to nine weeks, were anesthetized and shaved from the neck to the base of the tail. The harvested hair was sterilized, washed with non-ionic detergent, and carefully washed with isotonic salt solution.

After using a sterile preparation solution, a horizontal incision was made on the dorsal skin halfway between the base of the neck and the tail. Through this incision, a small pocket was made approximately two cm wide. The harvested hair was placed in the pocket, and the wound edges were closed with absorbable suture material. All rats were maintained on the same diet and fluid.

In Study II, utilizing ten purebred Lewis rats, the same protocol was followed to implant hair in a subcutaneous position.

In Study III, the same protocol was used with seven purebred Lewis rats to implant human hair in a subcutaneous position.

No rat showed signs of inflammation or infection at the area of the implant during the first three weeks. At three months, one rat showed an infection at the operative site, although it is believed that this was due to post operative trauma such as a bite from another rat. At six months after the implant, the rats were active without any detected abnormalities. The volume of the implants has been maintained.

The implant is soft, spongy, mobile, and is not adhered to the deep layers of tissue. Serial measurements of the implants have not revealed any significant differences when compared to the initial measurements. There has been no evidence of deformity or flattening of the pockets.

Two of the rats were sacrificed after hematological studies, which did not reveal any abnormalities. The implants were evaluated macroscopically and microscopically. Macroscopically, the implants were forming a fine mesh of hair without any adhesions to the skin above or the aponeurosis beneath it. There was no evidence of resorption or substitution by fibrotic material. No nodules or foreign body granulomas were evident on macroscopic evaluation.

Histologic studies were done, and the implant hairs did not show any difference when compared to the exterior hairs of the animal. Stain showed areas of lymphocytic infiltration and isolated cellular debris. The mesh of the implants was formed by abundant collagen fibers mixed in with hair shafts. Some isolated fibroblast was present with rare lymphocytes, plasmocytes, and polymorphonuclear cells. No microscopic evidence of invasion of the mesh of collagen to any close structure was noted. The skin surrounding the implant did not exhibit any abnormalities, and none was noted in the adjacent aponeurosis.

Consequently, hair, properly harvested and prepared, is seen as a viable biological replacement material which does not seem to suffer rejection when placed internally of the body.

While we have shown our invention in one form, it will be obvious to those skilled in the art that it is not so limited but is susceptible of various changes and modifications without departing from the spirit thereof.

What we claim is:

1. A biological replacement material for use in soft tissue replacement procedures comprising a predetermined quantity of harvested hair, wherein said hair is sterilized and washed in a non-ionic detergent, washed in an isotonic salt to eliminate micro-organism bacteria, and chopped into strands of a predetermined length wherein said strands form a non-woven mass suitable for insertion within a biological cavity such that said cavity is filled with said mass.

2. A replacement material as defined in claim 1 wherein said hair is confined within a physiologically degradable confinement vehicle for implantation.

3. A replacement material as defined in claim 1 wherein said hair is autologous.

4. A biological replacement material for use in soft tissue replacement procedures comprising a predetermined quantity of harvested hair, wherein said hair is sterilized and washed in a non-ionic detergent, washed in an isotonic salt to eliminate micro-organism bacteria, cut into suitable lengths and formed into elongated woven strands with said hair lengths oriented substantially along a longitudinal axis of said elongated woven strands.

5. A replacement material as defined in claim 4 wherein said hair is autologous.

6. A biological replacement material for use in soft tissue replacement procedures comprising a predetermined quantity of harvested hair, wherein said hair is sterilized and washed in a non-ionic detergent, washed in an isotonic salt to eliminate micro-organism bacteria, cut into suitable lengths and formed into elongated woven strands with said hair lengths oriented substantially along a longitudinal axis of said elongated woven strands; and strands of a physiologically degradable material are interwoven with said hair lengths and oriented along said elongated woven strands.

7. A replacement material as defined in claim 6 wherein said hair is autologous.

8. A biological replacement material for use in soft tissue replacement procedures comprising a predetermined quantity of harvested hair, wherein said hair is sterilized and washed in non-ionic detergent, washed in an isotonic salt to eliminate micro-organism bacteria, and woven into a fabric with said hairs oriented transversely and longitudinally therein.

9. A replacement material as defined in claim 8 wherein said hair is interwoven with strands of physiologically degradable material to form said fabric.

10. A replacement material as defined in claim 8 wherein said hair is autologous.

* * * * *